US005727186A

United States Patent [19]
Shervington et al.

[11] Patent Number: 5,727,186
[45] Date of Patent: Mar. 10, 1998

[54] SIMULATION APPARATUS AND GAS DISPENSING DEVICE USED IN CONJUNCTION THEREWITH

[75] Inventors: Evelyn Arthur Shervington, Nr Petersfield; Raymond Cyril Burningham, Morden, both of England

[73] Assignee: The BOC Group plc, Surrey, England

[21] Appl. No.: 379,131

[22] Filed: Jan. 27, 1995

[30] Foreign Application Priority Data

Feb. 1, 1994 [GB] United Kingdom ............... 9401899
Sep. 17, 1994 [GB] United Kingdom ............... 9418797

[51] Int. Cl.⁶ ..................... G06F 9/455; G06F 17/00
[52] U.S. Cl. ............ 395/500; 364/578; 364/221.2; 364/227.1; 364/DIG. 1
[58] Field of Search ................... 395/500; 364/578

[56] References Cited

U.S. PATENT DOCUMENTS 3,628,829 12/1971 Heilig ........................... 297/217.4
4,603,030 7/1986 McCarthy .......................... 422/4
4,629,604 12/1986 Spector .......................... 422/124
5,393,074 2/1995 Bear et al. ...................... 273/440
5,486,141 1/1996 Ohga et al. ....................... 472/60

FOREIGN PATENT DOCUMENTS 1356435 6/1974 United Kingdom.
2254930 10/1992 United Kingdom.

OTHER PUBLICATIONS

WPI Abstract Acc No. 92-023204/03 Dec. 25, 1991.
WPI Abstract Acc No. 84-177169/29 May 31, 1984.

Primary Examiner—Kevin J. Teska
Assistant Examiner—Ayni Mohamed
Attorney, Agent, or Firm—R. Hain Swope; David A. Draegert

[57] ABSTRACT

Simulation apparatus for displaying three-dimensional graphics including a device for emitting an aroma generating material in connection therewith and a dispensing apparatus for emitting the aroma generating material.

7 Claims, 3 Drawing Sheets

FIG. I

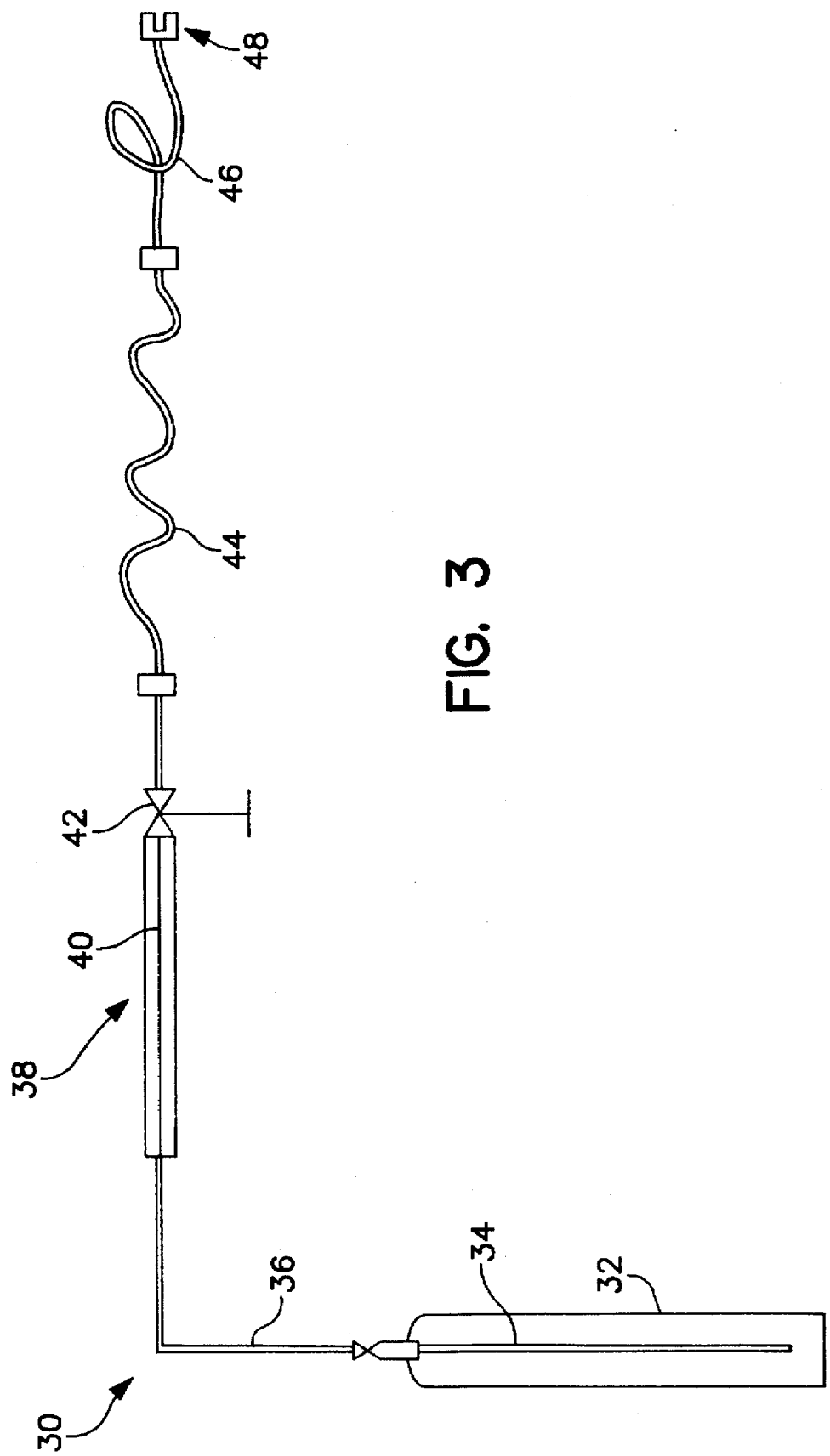

SIMULATION APPARATUS AND GAS DISPENSING DEVICE USED IN CONJUNCTION THEREWITH

TECHNICAL FIELD

The present invention is generally directed to a simulation apparatus for displaying three-dimensional graphics in which an aroma generating material is injected through the simulation apparatus to be sensed by the user and generally to a dispensing apparatus for emitting the aroma generating material.

BACKGROUND OF THE PRIOR ART

Virtual reality systems generally include a computer control module, a headset and a joy stick and/or gloves worn by the user to allow "participation" in the virtual reality graphics. Three-dimensional computer graphics are viewed inside the headset. A signal corresponding to the three-dimensional graphics is created by a computer module and the signal is transmitted to the headset where it is translated into a three-dimensional graphic display.

For example, the three-dimensional graphics can be in the form of a race track. Computerized images of vehicles move along the track. The speed and direction of the vehicles can be controlled by the user through the joy stick and/or gloves. The view of the race track can therefore be changed with every movement of the users headset and/or joy stick/gloves.

It is also known to fit the headset with sound through a stereo system. Movement of the headset can be used to change the volume and/or direction of sound to simulate the noise of a vehicle as it moves along the race track.

Virtual reality systems are dependent on involving the senses of the user. As described above current virtual reality systems involve the user's visual, auditory and tactile senses. It would be a significant advance in the art of virtual reality to devise a system which involves the user's olfactory senses and to provide a device which can generate and deliver an aroma generating material, especially for use in virtual reality systems.

The delivery of an aroma generating material such as a fragrance in the form of an atomized liquid spray is known. It is also known to incorporate a fragrance into a solid matrix such as soap or plastic pellets. Additionally, it is known to incorporate a fragrance into an oil based solvent and to heat the solution or to dissolve the fragrance in alcohol or water and to disperse the resulting solution by forced evaporation with a fan of wicks.

Each of these methods, however, suffer from a number of disadvantages. For example, atomized sprays are disadvantageous because they do not allow precise control of the amount of the fragrance which is released. Solid matrices do not offer a consistent rate of dispersal and are highly dependent on temperature, humidity and the amount of fragrance in the solid matrix both initially and over time.

Oil based solvent compositions are limited because the fragrance may oxidize and/or boil-off thereby affecting the quality of the aroma. Other solvent based systems (e.g.alcohol and water) are disadvantageous because of changes to the fragrance due to oxidation and limited control over the dispersal rate of the fragrance.

The above-mentioned problems with existing dispensing systems occur because the aroma generating materials are typically complex and highly volatile. They can easily oxidize resulting in a change or loss of the desired aroma.

The aroma generating materials may contain ten or more different aromatic components with different boiling points and rates of evaporation. Each material can therefore be expected to emit an aroma at a different rate and be susceptible to degradation under different conditions and rates of time.

It would therefore be a significant advance in the art of dispensing an aroma generating material including within the environment of a simulation apparatus, such as virtual reality systems, if the material could be dispensed at a controlled rate in a preselected location.

SUMMARY OF THE INVENTION

The present invention is directed in part to a simulation apparatus and method, particularly an apparatus and method which creates the effect of virtual reality. The present invention provides for the generation of an aroma as part of the virtual reality effect. In addition, the present invention is directed to a dispensing apparatus which can generate and deliver an aroma generating material to be sensed by the user so as to involve the user's olfactory senses during operation.

More specifically, the present invention encompasses in part a simulation apparatus comprising:

a) Computer graphics signal receiving means for receiving a signal for displaying three-dimensional computer generated graphics corresponding to said signal;

b) a computer control module for generating said signal and for transmitting said signal to the receiving means; and c) aroma generating means for releasing an aroma generating material and for transmitting the aroma generating material through the receiving means for sensing by the user of the simulation apparatus.

In another aspect of the invention there is provided a dispensing apparatus for dispensing an aroma generating material comprising:

a) at least one source of an aroma generating material;

b) a first conduit operatively connected to the at least one source of the aroma generating material;

c) restriction means in the first conduit for controlling the flow of the aroma generating material therethrough;

d) a second conduit operatively connected to the restriction means for transporting the aroma generating material from the restriction means to a nozzle;

e) temperature raising means for raising the temperature of the aroma generating material between the restriction means and the nozzle; and f) a nozzle for emitting the aroma generating material.

BRIEF DESCRIPTION OF THE DRAWINGS

The following drawings illustrate embodiments of the invention and are not intended to limit the invention as encompassed by the claims forming part of the application.

FIG. 3 is a schematic view of an embodiment of the dispensing apparatus of the present invention.

DETAILED DESCRIPTION OF THE INVENTION

The present invention is in part directed to a simulation apparatus, as, for example, a device for producing virtual reality images. The apparatus is provided with a system for generating and delivering an aroma generating material in proximity to the simulation apparatus. The aroma produced thereby corresponds to the aroma that would be expected if the computer generated graphics were real.

The aroma generating material includes any compound or formulation that produces an aroma (i.e. aromatic substance) such as, for example, fragrances, scents, odors and the like. The aroma generating material also includes a solvent, as for example carbon dioxide, alkanols such as methanol and ethanol, and nitrous oxide. As will be explained in detail hereinafter the solvent is a liquid when compressed but vaporizes when the pressure on the liquid is reduced.

Figure 1:
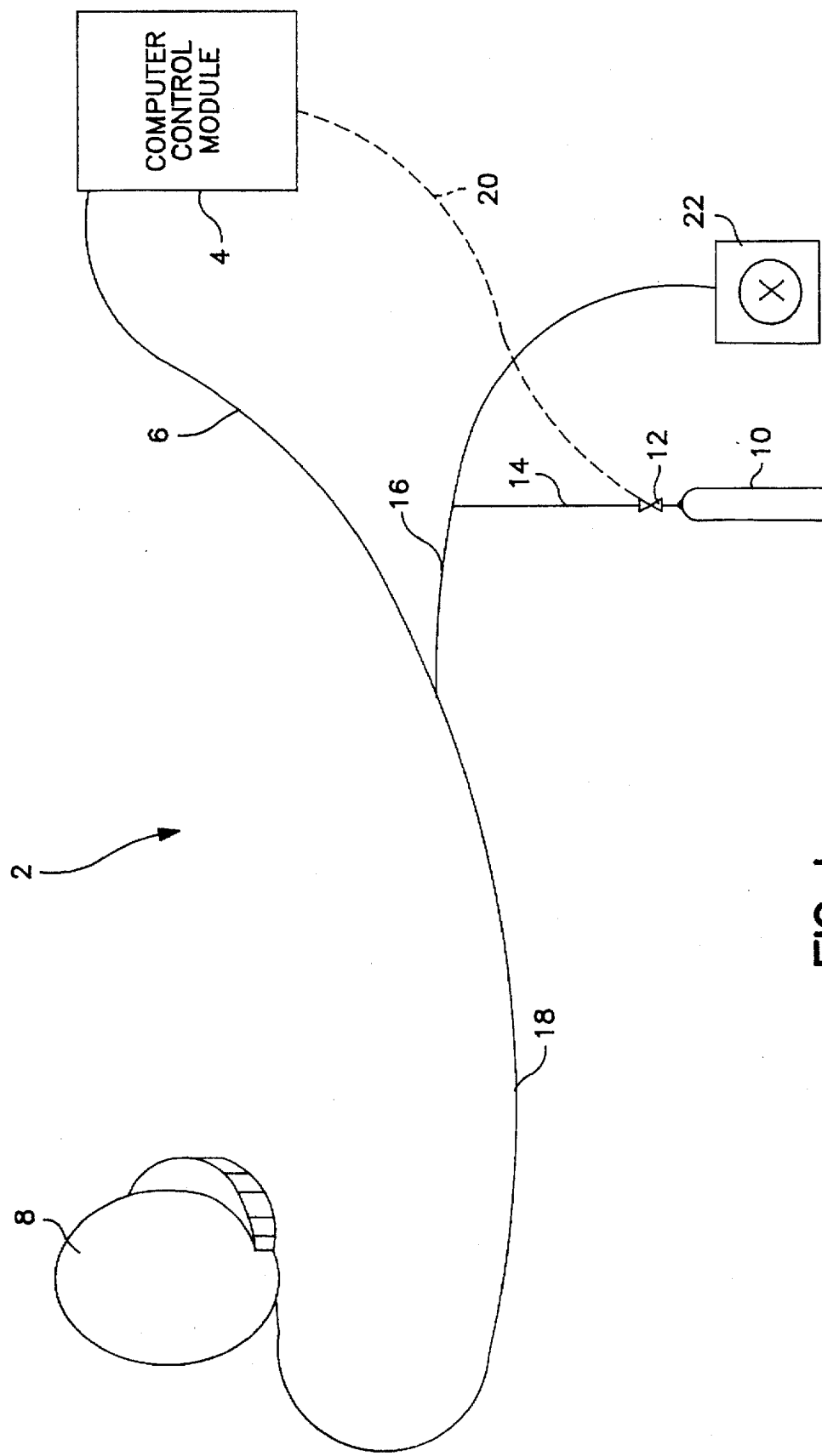
FIG. 1 is a schematic view of a first embodiment of a simulation apparatus according to the invention.

Referring to FIG. 1 there is shown a simulation apparatus 2 for use as, for example, a "virtual reality" computerized entertainment system. The apparatus 2 includes a computer control module 4 capable of generating a signal corresponding to desired computer graphics and for transporting the signal through a cable line 6 to a receiver which, as shown in FIG. 1, is in the form of a headset 8 as is well known in the art. The headset 8 includes a display device (not shown) which enables the user to view the computerized images which comprise the virtual reality display.

In accordance with the present invention, an aromatic substance is provided in proximity to the headset 8 to form part of the virtual reality effect. More specifically, an aroma generating material is supplied from a source 10. The compressed fluid, typically in the form of a liquid and containing the aromatic substance dissolved in the solvent is stored in the cylinder 10 until ready for use at a pressure of typically about 50 bar.

The flow of the aroma generating material from the cylinder 10 is controlled by a solenoid valve 12. Once released from the cylinder 10 by the opening of the valve 12, the compressed fluid is depressurized to form an aroma generating material in the form of a gas which enters a conduit 14 and flows therethrough to a conduit 16 and then to a conduit 18, which is coaxial with the cable 6, to the headset 8.

It is desirable to control the concentration of the aroma generating material that is transported to the headset 8. If the concentration of the aroma generating material is too great, the user may experience discomfort. One manner of controlling the concentration of the aroma generating material is to intermittently release the aroma generating material from the cylinder 10. This may be accomplished by opening the valve 12 for preselected periods of time to allow a bolus or pulse of the aroma generating material to enter the conduit 14 at periodic intervals. Automatic control of the number of boluses and their duration may be accomplished by controlling the valve 12 through a conventional timing device (not shown) associated with the computer module 4, via a cable line 20. The bolus of aroma generating may receive an assist by sending a pressurized stream of gas (e.g. air) from a compressor 22 through the conduits 16 and 18.

It may be desirable to purge the conduits 16 and 18 of residual aroma generating material after each bolus of the material has been provided to the headset 8. This may be accomplished as shown in FIG. 1 by sending another pressurized stream of gas from the compressor 22 through the conduits 16 and 18. The pressurized gas produced by the compressor 22 may be intermittently supplied to the conduits 16, 18 by employing a timing device (not shown) operatively connected to the computer module 4 in a known manner. The compressor 22, through the release of the pressurized stream of inert gas, also serves to provide cooling gas to the headset to make the user more comfortable.

The simulation apparatus 2 of the present invention may be provided with multiple sources of the aroma generating material. This system is advantageous because it enables a greater quantity of the aroma generating material to be made available between refills. In addition, it allows more than one aroma generating material (e.g. different fragrances) to be transported to the headset to further enhance the virtual reality effect.

Figure 2:
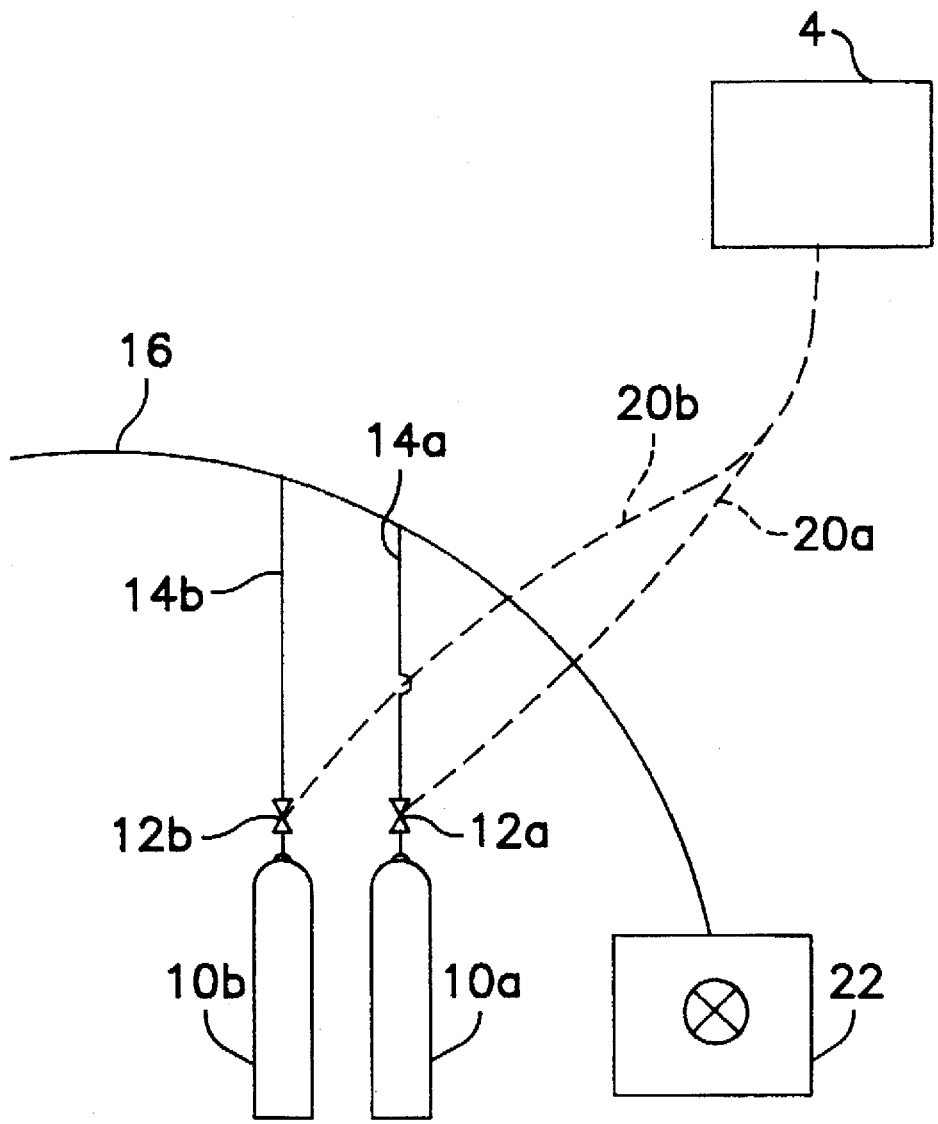
FIG. 2 is a partial schematic view of another embodiment of the simulation apparatus of the invention using multiple sources of an aroma generating material.

Referring to FIG. 2, there are shown two cylinders 10a and 10b, each connected to respective conduits 14a and 14b through respective solenoid valves 12a and 12b. The operation of each of the dual cylinders 10a, 10b is the same as described in connection with the cylinder 10 in FIG. 1. Automatic operation of the solenoid valves 12a and 12b is accomplished through cables 20a and 20b. When each cylinder 10a and 10b contains a different aroma generating material, the pressurized gas from the compressor 22 can entrain each bolus of the aroma generating material transported from the conduits 14a, 14b. Alternatively, a single conduit can be used to connect the cylinders 10a, 10b to the headset 8 (see FIG. 1). In this embodiment the various boluses of the aroma generating materials follow each other through the conduits 14, 16, 18.

It will be understood that reference has been made herein to a simulation apparatus which can be used for enjoyment (e.g. virtual reality video games). The present simulation apparatus is also applicable to occupational training devices and the like such as, for example, flight simulators for the training of pilots.

The present invention is also directed to a dispensing apparatus capable of dispensing an aroma generating material to a pre-selected location such as a headset.

Referring to FIG. 3 there is shown a dispensing apparatus 30 including at least one cylinder 32 for storing an aroma generating material under pressure such as about 50 bar. The aroma generating fluid as previously described contains an aromatic substance (e.g. fragrance) dissolved in a solvent such as liquid carbon dioxide, alkanols, nitrous oxide, and the like.

Extending substantially through the length of the cylinder 30 is a dip tube 34 which is connected to a conduit 36 which includes a restrictive throttle 38 for the aroma generating material passing therethrough. As shown specifically in FIG. 3 the restrictive throttle 38 is in the form of a small bore tube 40 of predetermined length. The dimensions of the tube will vary according to the desired restriction of the aroma generating material. Typically the small bore tube 40 has a diameter of about 0.019 inches and a length of about 6 inches.

Downstream of the restriction throttle 38 is a solenoid valve 42 which may be operated manually or by a computer as previously described in connection with FIGS. 1 and 2. The solenoid valve 42 enables boluses of the aroma generating material to be transmitted to the desired location.

In accordance with the present invention, the temperature of the aroma generating material transmitted through the restriction throttle 38 is thereafter raised. In one embodiment of the invention heat is imparted to the aroma generating material through heat conductive metal tubing 44, such as copper tubing. The tubing 44 separates the conduit 36 from a conduit 46 which in turn is connected to a nozzle 48 and enables the aroma generating material to be heated sufficiently to prevent freezing.

The diameter of the second conduit 46 is similar to that of the small bore tube 40 although the length is typically shorter (e.g. about one inch). Thus the conduit 46 serves as a second throttle of the aroma generating material as it passes through the dispensing apparatus 30.

In operation of the dispensing apparatus, the valve 42 controls the flow of the aroma generating material from the cylinder 32 through the conduit 36 and the small bore tube 40. As previously explained the valve 42 can be operated to provide discreet short boluses of the aroma generating material. The tube 40 acts as a restrictive throttle to insure that the aroma generating material passes slowly through the system to provide a relatively small cross-sectional area of the aroma generating material at the inlet to the valve 42.

The valve 42 may be controlled by a timing device (not shown) which provides a bolus of the aroma generating material at a given frequency and duration thereby insuring precise control of each bolus passing through the valve 42.

The conduit 46 and the nozzle 48 together act as a further throttle to insure the spread of each bolus of the aroma generating material into a pre-selected location and to minimize noise by slowing the flow rate thereof.

The flow rate of the aroma generating material through the dispensing apparatus will depend on such factors as 1) the solubility of the aromatic substance in the solvent 2) the viscosity of the aroma generating material 3) the amount of heat applied to the aroma generating material through the metal tubing and 4) the degree to which the tube 40 and the conduit 46 coupled with the nozzle 48 serve to restrict the flow of the aroma generating material from the cylinder 32 to the desired location.

The size of the small bore tubes and the amount of heat needed to be applied will depend on the viscosity of the aroma generating material. The diameters of the respective tubes will vary. If the bore tube can more o small then blockage in the tube can more easily occur. If the diameter of the bore is too large then the size of the bolus and therefore the amount of the aroma generating material cannot be controlled in a desired manner.

We claim:

1. A simulation apparatus comprising:

(a) computer graphics signal receiving means for receiving a signal for displaying three-dimensional computer-generated graphics corresponding to said signal;

(b) a computer control module for generating said signal and for transmitting said signal to the receiving means;

(c) aroma generating means for providing an aroma generating material in the form of a gas at the receiving means, said aroma generating means comprising at least one source of compressed aroma generating material in the form of a liquid, valve means for releasing the aroma generating material under reduced pressure to form said gas and a conduit for transporting said gas to the computer graphics signal receiving means, said valve means being operable at varying intervals and durations in response to signals from the computer control module, and (d) automatic control means operatively connected to said computer control module for automatically controlling said valve means.

2. The simulation apparatus of claim 1 wherein said liquid comprises an aromatic substance dissolved in a solvent.

3. The simulation apparatus of claim 2 wherein the solvent is selected from the group consisting of carbon dioxide, an alkanol and nitrous oxide.

4. The simulation apparatus of claim 1 further comprising compressed gas generation means for generating a flow of compressed gas and transporting the flow of gas through the conduit to assist the flow of the aroma generating material or to remove the aroma generating material from the conduit.

5. The simulation apparatus of claim 4 wherein said conduit includes a restriction means for reducing a passageway for the flow of the aroma generating material and, downstream of said conduit, valve means for controlling the flow of the aroma generating material therefrom, temperature raising means for raising the temperature of the aroma generating means, a second conduit for receiving the aroma generating material including a restriction means, and a nozzle for emitting the aroma generating material.

6. The simulation apparatus of claim 4 wherein the compressed gas is compressed air.

7. The simulation apparatus of claim 1 wherein the computer graphics signal receiving means is a headset.

* * * * *